United States Patent [19]
Tremont et al.

[11] Patent Number: 5,827,925
[45] Date of Patent: Oct. 27, 1998

[54] POLYMERIC DRUG DELIVERY SYSTEM

[75] Inventors: Samuel J. Tremont, Manchester, Mo.; Paul Waddell Collins, Deerfield, Ill.; William Eldredge Perkins, Libertyville, Ill.; Peter Hadley Jones, Bull Valley, Ill.

[73] Assignee: Monsanto Company, St. Louis, Mo.

[21] Appl. No.: 966,171

[22] PCT Filed: Jul. 22, 1991

[86] PCT No.: PCT/US91/05029

§ 371 Date: Jan. 25, 1993

§ 102(e) Date: Nov. 2, 1993

[87] PCT Pub. No.: WO92/01477

PCT Pub. Date: Feb. 6, 1992

[51] Int. Cl.$^6$ ....................................................... C08F 8/00
[52] U.S. Cl. .................. 525/102; 424/78.17; 424/78.18; 424/78.27; 515/332.8; 515/332.9; 515/333.1; 515/333.2; 515/342; 515/379

[58] Field of Search ................................. 525/102, 332.8, 525/332.9, 33.1, 333.2, 342, 379; 424/78.17, 78.18, 78.27

[56] References Cited

U.S. PATENT DOCUMENTS

| | | | |
|---|---|---|---|
| 4,489,056 | 12/1984 | Himmelstein et al. | 424/22 |
| 4,764,364 | 8/1988 | Heller et al. | 424/78 |
| 5,474,767 | 12/1995 | Tremont | 424/78.27 |

*Primary Examiner*—Bernard Lipman
*Attorney, Agent, or Firm*—Roger A. Williams

[57] ABSTRACT

A drug delivery system adapted to release an effective amount of a drug at pH values of about 1 to 7 without releasing a significant amount of the drug at pH values of about 7 and above, the system comprising a polymeric material and a drug covalently bonded to the polymeric material through a pH sensitive covalent bond capable of being cleaved in the pH range of 1 to about 7.

31 Claims, 1 Drawing Sheet

POLYMERIC DRUG DELIVERY SYSTEM

BACKGROUND OF THE INVENTION

1. Field of the Invention

This invention relates to oral drug delivery systems for site specific drug delivery. More particularly, the present invention relates to drug delivery systems wherein a drug is covalently bound to a polymeric material for site specific delivery of the drug based upon the pH of the site wherein the drug is to be delivered. The present invention is especially directed to a delivery system for delivering a drug in an environment exhibiting a pH of up to about 7 such as can be found in the gastric system.

2. Prior Art

Various approaches are disclosed in the prior art for achieving controlled oral delivery of drugs. The majority of such approaches are directed to sustained release in vivo and utilize a polymeric material as a carrier, coating or rate-limiting barrier such as a membrane. One sustained release delivery system utilizes chemical bonds to control release. Ferruti et al, U.S. Pat. No. 4,228,152, disclose a polymeric sustained release prostaglandin delivery system wherein a prostaglandin is directly bonded or bonded through an oxyalkylenic, aminoalkylenic, or oxyaminoalkylenic chain to a polyacrylic or polymethacrylic backbone. Upon entry into the body, the prostaglandins are reported to be gradually hydrolyzed causing release thereof into the body over sustained time intervals.

Few systems, however, are directed at localized drug delivery wherein the delivery of a drug is confined to a particular tissue or organ. One such system is disclosed by Saffron, in U.S. Pat. No. 4,663,308. Saffron discloses a polymeric drug delivery system for localized drug delivery wherein a drug is coated with a polymer which is crosslinked with an azo compound. The azo bonds are reported to be reduced by azo reductases existing in the large intestine causing the polymer coating to degrade, thereby releasing the drug into the large intestine. Another of such systems is disclosed by Siegel et al in J. Controlled Release, 8, 179–182 (1988). Siegel et al disclose hydrophobic polyamine hydrogels useful for regional drug delivery at nonneutral pH values.

SUMMARY OF THE INVENTION

The present invention is directed to localized drug delivery through oral administration of an acidic pH-dependent drug delivery system. One aspect of the subject drug delivery system involves release of a drug in an acidic environment such as in a gastric environment which typically has a pH value ranging from about 1 to about 4. In this system, the drug can be covalently bonded to the polymer backbone or to a pendant functional group on the polymer backbone and can be released from the polymer by hydrolytic cleavage of the covalent bond at a pH below about 7. The drug can be incorporated into the polymer by way of a pH-sensitive linker to which the drug can be covalently bonded which covalent bond is cleaved at pH values of less than about 7 but not at higher pH values. Thereby release of the drug at such higher pH values, such as about 7 or higher, is inhibited. In another aspect, the present drug delivery system involves methods of covalently bonding drugs to polymeric materials by way of chemical linkers, and particularly involves methods for incorporating drugs into polymers by way of acid-sensitive linkers.

In another aspect of the invention herein, the polymeric material can be adapted to swell at pH values of about 1–7 to enhance release of an effective amount of the drug. The drug can be covalently bonded to the polymer as described above through a pH-sensitive linker such that when the polymer swells upon exposure to the acid environment, the release of the drug into the gastric environment is facilitated.

More particularly, the invention herein is directed to a delivery system for releasing an active ingredient at pH values up to about 7 and for inhibiting release of the active ingredient at pH values above 7. The delivery system includes a polymeric material covalently bonded to the active ingredient through a silyl bond that is pH sensitive and capable of being cleaved at pH values up to about 7.

BRIEF DESCRIPTION OF THE DRAWINGS

The invention herein can be understood with reference to the following Detailed Description and the accompanying drawing of FIG. 1 which is a graph illustrating the comparative pharmacokinetic properties (plasma concentration) of a delivery system herein wherein the drug misoprostol is delivered to male rats compared to a pharmaceutical composition containing non-covalently bound misoprostol. The graph is a plot of the concentration of misoprostol free acid in picograms per milliliter versus time in hours.

DETAILED DESCRIPTION OF THE INVENTION

The present invention relates to site specific drug delivery systems for delivering a drug to the gastric system, namely the stomach, wherein a drug is covalently bonded to a polymeric material adapted to release an effective amount of the drug at pH values of less than about 7 without releasing any significant amount of the drug at higher pH values.

More particularly, the invention herein is directed to a delivery system for releasing an active ingredient in the stomach at pH values of 1 to about 4 and for inhibiting release of the active ingredient at pH values above 7. The delivery system includes a polymeric material covalently bonded to the active ingredient through a covalent bond that is pH sensitive and capable of being cleaved at pH values up to about 4.

In an especially preferred embodiment of the invention herein, the polymeric materials are adapted to swell at pH values of about 1–7 with release of an effective amount of the drug. The polymeric materials which exhibit such swelling characteristics are especially preferred for use in delivering the active ingredient to the stomach as the swelling of the polymer can provide a greater opportunity for the active ingredient to be exposed to the acidic conditions of the stomach and thereby cleaved and released from the delivery system.

More particularly, the invention herein is directed to a delivery system for releasing an active ingredient in the stomach at pH values of 1 to about 4 and for inhibiting release of the active ingredient at pH values above 7 and which system exhibits swelling at such a pH range. The delivery system includes a swellable polymeric material covalently bonded to the active ingredient through a covalent bond that is pH sensitive and capable of being cleaved at pH values up to about 7.

The invention herein also includes a polymeric delivery system wherein the polymer can be modified by attachment of auxiliary groups which can impart or enhance certain properties such as gastric retention, hydrophilicity, crystallinity, swellability and the like, which properties can effect the rate of release of the drug. For example, auxiliary groups such as dialkylamino groups or quaternized ammonium salts can be employed to impart or enhance such properties.

The terms "drug" and "active ingredient" are used interchangeably herein and are used to describe a compound that is to be delivered to a site in the body for release. The delivery system herein can include the incorporation of more than one active ingredient wherein it can be therapeutically beneficial to deliver or coadminister more than one active ingredient. Suitable drugs or active ingredients useful in the present invention include those generally classified as medicinal agents and which are adapted to be incorporated into the polymeric material and which form a pH sensitive (pH 1–7) covalent bond with the polymeric material. For example suitable active ingredients which can be used in the practice of the invention herein include compounds which contain an hydroxyl (—OH) group, a carboxylic acid group (—COOH), an amino group (—NH$_2$ or an —NHR group wherein R is an alkyl group of 1–4 carbons), a thiol group (—SH), or an enolizable carbonyl group (i.e., aldehydes, ketones and amides).

Exemplary active ingredients are those medicinal agents wherein gastric release is preferred over intestinal release or wherein control of the rate of release of the active agent is desired for systemic action. For example, drugs in which delivery to the stomach is preferred include natural or synthetic prostaglandins and prostacyclins, (e.g., misoprostol, enisoprost, enprostil, iloprost, and arbaprostil) any drugs for the treatment of peptic ulcers, gastric antisecretory drugs, antimicrobial drugs, prokinetic drugs, cytoprotective drugs and the like. Exemplary antimicrobial drugs include tetracycline, metronidazole and erythromycin which can be used for eradication of gastric microbes such as Heliobacter pylori which may cause or contribute to gastric ulceration. The antimicrobial agents comprise a class of active ingredients for which it can be therapeutically beneficial to deliver more than one such antimicrobial agent by using the delivery system herein due to the differences in the antimicrobial efficacy spectrum of each agent. Active ingredients also include systemically acting agents which do not directly act in the stomach but which can be readily delivered to the stomach for controlled release, absorption and systemic action. Examples of such drugs are those drugs which have a relatively short duration of action for which sustained plasma levels of active ingredient is desired.

The delivery system herein is especially useful in delivering active ingredients that are prostaglandin analogues of the structure -continued
or wherein R represents hydrogen or lower alkyl having 1 to 6 carbon atoms; R$_1$ represents hydrogen, vinyl or lower alkyl having 1 to 4 carbon atoms and the wavy line represents R or S stereochemistry; R$_2$, R$_3$, and R$_4$ are hydrogen or lower alkyl having 1 to 4 carbon atoms or R$_2$ and R$_3$ together with carbon Y form a cycloalkenyl having 4 to 6 carbon atoms or R$_3$ and R$_4$ together with carbons X and Y form a cycloalkenyl having 4 to 6 carbons and wherein the X–Y bond can be saturated or unsaturated.

Particularly preferred prostaglandins include the prostaglandin analogue misoprostol, (±) methyl 11α, 16-dihydroxy-16-methyl-9-oxoprost-13E-en-1-oate of the following structural formula Another prostaglandin analogue which can be delivered by the system herein is enisoprost, (±) methyl 11α,16-dihydroxy-16-methyl-9-oxoprost-4Z,13E-diene-1-oate, which has the following structural formula Another prostaglandin analogue which can be delivered by the system herein is the prostaglandin analogue which has the following structural formula The active ingredient is present in the compositions of this invention in an amount that is sufficient to prevent, cure and/or treat a condition for a desired period of time for which the composition of this invention is to be administered, and such an amount is referred to herein as "an effective amount." As is well known, particularly in the medicinal arts, effective amounts of medicinal agents vary with the particular agent employed, the condition being treated and the rate at which the composition containing the medicinal agent is eliminated from the body, as well as varying with the subject in which it is used, and the body weight of that subject. An effective amount is that amount which in a composition of this invention provides a sufficient amount of the active ingredient to provide the requisite activity of the active ingredient in the body of the treated subject for the desired period of time, and can be less than that amount usually used.

Inasmuch as amounts of particular active ingredients that are suitable for treating particular conditions are generally known, it is a relatively easy laboratory task to formulate a series of release compositions of this invention containing a range of such active ingredients to determine the effective amount of such an active ingredient for a particular composition of this invention. Based upon a reading of the description herein and of the following examples, it is within the skill of the art to select an amount of any particular active ingredient and to covalently bond such an amount to a polymer herein described for delivering an effective amount of such active ingredient. While the effective amount for all active ingredients cannot be stated, typical compositions of this invention can contain about one microgram to about one gram of active ingredient per dose administered. More preferably, a composition of this invention can contain about one microgram to about 250 milligrams per dose.

The drugs or medicinal agents can be covalently bonded to a polymeric material according to the teachings of the present invention for release in an acidic environment depending on the desired physiological action of the drug, systemic side effects associated with each drug, decomposition rate of the drug in a particular environment and other factors well known in the medicinal arts.

For delivery of a drug to such an acidic environment, suitable polymeric materials are those which are capable of forming a covalent bond with the active ingredient or which are capable of being adapted to form a covalent bond with the active ingredient wherein the covalent bond is pH sensitive and capable of being cleaved at pH values of up to about 7. Polymeric materials which themselves cannot form such a covalent bond can be modified by attaching a linker group to such polymer. The linker group can be any suitable compound which can bond to both the polymer and the active ingredient. A covalent bond can be formed between the active ingredient and such attached linker group or the active ingredient can be covalently bonded to a linker group and the linker group/active ingredient attached to the polymer.

Covalent bonds that can be cleaved under acidic conditions include bonds of the following types: silyl ethers and esters, acetals, thioacetals, imines, aminals, carbonates, and vinyl ethers. A preferred covalent bond that can be cleaved within the preferred pH range is a silyl ether covalent bond. Silyl ether covalent bonds are especially preferred because such a bond can be formed between a silyl functional group on the polymer (or linker group) and any hydroxyl functional groups on the active ingredient.

It is preferable that the polymeric materials chosen for the practice of the invention herein are nonabsorbable or essentially nonabsorbable in the patient's body. Such polymeric materials are not absorbed or metabolized by the body and thereby are beneficial for use as a drug "carrier" as such polymers are substantially physiologically inactive. For example, polymers which are of high molecular weight, e.g., 1,000–160,000 $M_w$, charged or crosslinked polymers or polymers which are insoluble under physiologically acidic conditions (such as by crosslinking), eliminate or significantly reduce transportation of the polymer across the gut wall. Exemplary polymeric materials include polyamines, polybutadienes, copolymers of 1,3-dienes, polysaccharides, hydroxypropylmethylcellulose, and polymers of acrylic and methacrylic acid including copolymers thereof, maleic copolymers, and any polymer having derivatizable olefinic bonds. The term "copolymer" is used herein to mean mixed polymers (such as polybutadiene) which contain more than one polymer. A preferred polymer is a polymer selected from polyamine, polybutadiene, copolymers of 1,3-dienes and any polymer having a derivatizable olefinic bond. An especially preferred polymer is a polymer which is a functionalized polybutadiene containing amino functional groups. Such a polymer is preferred because the amino functional groups are capable of bonding with an active ingredient or a linker group. For example, for an amino functionalized polybutadiene, a chlorodimethylsilane linker and active ingredient containing a hydroxyl group form a silyl ether bond wherein cleavage can occur in a pH range of about 1 to 5.

Another group of preferred polymeric materials includes polymers which are adapted to swell at pH values of about 1 to 7. Polymers which can swell in the desired pH range for cleavage of the covalent bond, enhance the cleavage of such bonds and thereby the release of an effective amount of the drug. Exemplary polymeric materials which manifest such swelling characteristics include polyamines and their quaternary salts.

In order to render certain of such polymers insoluble under acidic conditions, the polymers can be crosslinked by methods well known in the art. For example, crosslinking agents can be employed or free radical crosslinking of the polymer can be performed. The crosslinking is performed to an extent sufficient to render the polymer insoluble without significantly affecting the release characteristics of the polymer. Crosslinking is not necessary to make the polymer insoluble as solubility of the polymer can also be affected by the molecular weight of the polymer.

The crosslinking agent selected to be incorporated in the delivery system herein can be any suitable crosslinking agent which can crosslink the polymer selected for use in the system. The selection of a crosslinking agent is within the level of skill in the polymer art. Depending upon the polymer selected the crosslinking agent can be a dialdehyde, diacid, disilane, dihaloxylene, tri(halomethyl)benzene, dihaloalkane, dihaloalkene, diallylhalide, or any polyaromatic, aliphatic or allylic halide, and the like.

Certain of the polymers that can be used herein can also be modified by attaching auxiliary groups which can impart certain properties such as gastric retention, hydrophilicity, crystallinity and the like. For example, auxiliary groups such as dialkylamino groups or quaternized ammonium salts can be employed to control certain properties, such as hydrophilicity, swelling, crystallinity and the like to effect the drug release rate.

The drug is incorporated into the polymer by covalently bonding the drug to the polymeric material, such as to the polymer backbone or to certain pendant functional groups, by way of a covalent bond which can be cleaved to release an effective amount of the drug under physiological acidic conditions. The drug can be covalently bonded to the polymeric material by way of a chemical linker which covalent bond between the drug and the linker is hydrolytically cleaved under physiological acidic conditions to release an effective amount of the drug.

A pH-sensitive linker, as hereinafter defined, can be incorporated in the polymeric material to effect site specific delivery to an acidic environment. If a polymeric material is not capable of providing a pH-sensitive covalent bond with a drug, a drug delivery system for site specific delivery of a drug to a gastric environment can be made by utilizing a pH-sensitive linker from which the drug is hydrolytically cleaved under acidic conditions but not under basic conditions. That is, at pH values of greater than 7 there is little or no cleavage of the covalent bond to the active ingredient. Release of the active ingredient at pH values greater than 7 is thusly inhibited. The active ingredient is not released as it remains covalently bonded to the polymer at such higher pH.

Suitable linkers for incorporating an active ingredient into a polymeric material include pH-sensitive linkers which are cleaved at pH values of 1 to about 7 but not at pH values greater than about 7. For site specific delivery into an acidic environment, such linkers are acid-sensitive and preferably can be hydrolyzed at pH values of less than about 7. Exemplary linkers include acetal, thioacetal, imine, aminal, carbonate, vinyl ether, and silyl ether or ester type linkers. Preferred linkers for use in the system herein include pH-sensitive linkers selected from the group consisting of linkers formed utilizing chlorodiisopropylsilane, chloroisopropylethylsilane, chlorodimethylsilane, chlorodiphenylsilane, 1-(dimethylchlorosilyl)-2-(m,p-chloromethylphenyl)-ethane and 1,1,4,4-tetramethyl-1,4-dichlorodisilyl-ethylene. The more preferred linkers for use in the system herein are selected from chlorodiisopropylsilane or chloroisopropylethylsilane. Suitable linkers for incorporating a drug into a polymeric material wherein the drug is first bonded to the linker and the linker/drug is bonded to the polymer can include any suitable linker having the above noted functional groups and a functional group capable of bonding with the polymer. Two or more different linkers can be used to affect the overall rate of release of the drug from the polymer system herein.

A preferred linker for delivery of a drug into an acidic environment is one which forms a covalent bond by way of a silyl linker represented by the formula:

wherein P represents the polymeric material, Y can be O, or a COO— group from an —OH or —COOH group present on the active drug, and D represents a drug having an hydroxyl, carboxylic acid, or enolizable carbonyl group to form the Si—Y linkage and $R_1$ and $R_2$ independently represent H, substituted and unsubstituted alkyl, cycloalkyl, alkenyl, alkynyl, aryl, alkaryl or aralkyl radicals.

An especially preferred linker for delivery of a drug into an acidic environment is one which forms a covalent bond by way of a silyl ether linker represented by the formula:

wherein P represents the polymeric material, O is oxygen from a hydroxyl group present on the active drug, and D represents a drug having a hydroxyl group wherein the H is removed to form the Si—O ether linkage and $R_1$ and $R_2$ independently represent H, substituted and unsubstituted alkyl, cycloalkyl, alkenyl, alkynyl, aryl, alkaryl or aralkyl radicals. This preferred acid-sensitive linker is readily hydrolyzed at pH values of 1 to about 7 but at pH values of about 7 or more is not significantly hydrolyzed. Especially at the pH conditions in the body that are greater than 7, no significant hydrolysis occurs. Exemplary silyl ether type linkers include those which are formed utilizing chlorodiisopropylsilane, chloroisopropylethylsilane, chlorodimethylsilane, chlorodiphenylsilane, 1-(dimethylchlorosilyl)-2-(m,p-chloromethylphenyl)ethane, 1,1,4,4-tetramethyl-1,4-dichlorodisilylethylene, chlorophenylmethylsilane, chlorodiethylsilane, chloro(t-butyl)methylsilane, and chloroisobutylisopropylsilane.

These pH-sensitive linkers can also be utilized for incorporating a drug into a polymer that is adapted to swell at pH values of about 1 to 7 to further control delivery of the drug. Thus, an acid-sensitive linker can be utilized to covalently bond a drug to a polymeric material adapted to swell at pH values of about 1 to 7 with release of an effective amount of the drug.

A variety of methods can be utilized to covalently bond the drug to the polymer by way of the linker. For example, the linker can be a pendant functional group of the polymer to which the drug is bound; or the linker can be reacted with the drug and the linker/drug then bonded to the polymer or the linker can be reacted with the polymer and then the drug.

The polymer drug delivery system herein can be synthesized as generally described above and as shown in the general reaction/preparatory schemes shown herein. The General Scheme 1 illustrates a scheme for preparing a delivery system herein wherein a functional polymer is formed. A drug is attached to the functionalized polymer through a linker group. The linker group can be attached to the functionalized polymer prior to covalently bonding the drug (alternative step 1) or the linker group can be first covalently bonded to the drug and the linker/drug then attached to the functionalized polymer (alternative step 2). The polymer/drug system can be crosslinked but need not be if the polymer selected is of sufficient molecular weight to provide the desired insolubility and nonabsorbability.

The General Scheme 2 shows a reaction sequence for forming a functionalized polymer from a base polymer followed by crosslinking of the functionalized polymer. The active drug component can be attached by first attaching a linker group followed by the drug or the drug can be covalently bonded to the linker group prior to attaching the linker-drug to the crosslinked functionalized polymer.

In the following Scheme 3 a general sequence of steps is illustrated and in Scheme 4 a more specific sequence of steps is illustrated for forming a delivery system herein. The drug delivery system herein can be prepared in accordance with the schemes shown in these two reaction schemes. Scheme 3 shows that a polymer can be hydroformylated and reductively aminated to place a predetermined percentage of alkylamino functional groups on the polymer backbone. The extent (percentage) of amino functional groups can be selected and varied to vary the release rate of the active ingredient. The functionalized polymer is hydrosilylated and reacted with the drug to be covalently bound to the polymer. The polymer is crosslinked which can be followed by quaternization of any remaining alkylamino groups. R, R' and R" in the Scheme 3 can be alkyl, aralkyl, aryl or alkenyl.

Scheme 4 illustrates a more specific example. A polybutadiene of between about 1000 to 160,000 molecular weight ($M_w$) is functionalized by hydroformylation which is followed by reductive amination to place a predetermined percentage of dimethylamino functional groups on the polymer backbone. The resultant functionalized polymer is hydrosilylated and reacted at room temperature with the prostaglandin drug, misoprostol. This step covalently bonds misoprostol through a covalent silicon-oxygen bond to the C-11 hydroxy group on misoprostol. The polymer is crosslinked with α,α'-dichloro-p-xylene. The crosslinked polymer can be quaternized by quaternization of the remaining dimethylamino groups with methyl chloride.

GENERAL SCHEME 1

Base Polymer ⟶ Functional Polymer
(1) linker + drug or
(2) linker-drug
↓
[Functional Polymer]-[Linker]-Drug
crosslink
↓
Crosslinked{[Functional Polymer]-[Linker]-Drug}

GENERAL SCHEME 2

Base Polymer ⟶ Functional Polymer
crosslink ↓
Crosslinked[Functional Polymer]
linker ↓    ↓ linker-drug
Crosslinked[Functional Polymer]-Linker
drug ↓    ↓
Crosslinked[Functional Polymer]-Linker-Drug

SCHEME 3

SCHEME 4

Without further elaboration, it is believed that one skilled in the art can, using the preceding description, utilize the present invention to its fullest extent. The following preferred specific embodiments are illustrative of the invention herein.

The following examples 1–24 illustrate drug delivery systems according to the teachings of the present invention wherein an active ingredient is covalently bonded to a polymeric material with release of an effective amount of the active ingredient at pH values of about 1 to 7. The active ingredient is incorporated into the polymer by way of a pH-sensitive chemical linker.

EXAMPLE 1

This example illustrates a drug delivery system wherein misoprostol is incorporated into a polyamine by way of a silyl ether linkage. A linker group is attached to the polymer and the active ingredient, misoprostol, is covalently bonded to the polymer-linker system.

A 75 g sample of Polybutadiene (Aldrich 20,050-6 45% vinyl $M_w$=4500) was dissolved in 75 ml of toluene. Under a $N_2$ atmosphere this polymer solution was poured into a 300 ml autoclave. Next 3.3 g triphenylphosphine and 0.07 g of hydridorhodiumcarbonyltristriphenylphosphine were added to the clave under $N_2$. The clave was sealed and further degassed with $N_2$ by pressurizing the clave with 200 psi $N_2$ and then venting off the $N_2$ gas. The clave was heated to 80° C. under 400 psi $N_2$. After removing the $N_2$ the clave was charged with 300 psi 1:1 $CO/H_2$ at 80° C. The reaction was stirred at 1200 rpm until 0.917 moles of 1:1 $CO/H_2$ were reacted. After venting the clave, the polymer product was removed. The clave was washed with 100 ml of toluene and the washings were added to the polymer product. The product solution was concentrated to a 150 ml volume by means of a rotary evaporator. This polymer solution was slowly dripped into a solution containing 400 ml methanol and 100 ml water. The solution was allowed to separate into two phases and the top phase was removed by decantation. The bottom polymer phase was dissolved in 150 ml toluene and the above precipitation procedure was repeated. From this procedure 63.64 g of polymer product was isolated. $^1$H NMR indicated that 32% of the double bonds in the polybutadiene polymer [P(bd)] were hydroformylated.

A solution of the formyl-functionalized polymer (63.14 g) in 100 ml of sieved dried toluene and 20 ml methanol was placed in a two liter, 3-neck roundbottom flask equipped with a thermometer, addition funnel and a magnetic stir bar. The solution was further diluted with 500 ml of tetrahydrofuran and 40 ml of methanol. After cooling to 5° C. under nitrogen, 50 g of dimethylamine was added with stirring. After 15 minutes and by means of an addition funnel 85.8 ml of a 4.5M HCl/dioxane solution was slowly added to the solution. Finally, 17 g of sodium cyanoborohydride (sodium triacetoxy borohydride can also be used but does not require the use of the HCl/dioxane addition) was added by means of a funnel and rinsed into the flask with 20 ml of tetrahydrofuran. The solution was stirred for 40 hours and allowed to warm slowly to room temperature. The polymer solution was filtered after it was stirred with 60 ml of water for one hour. The filtrate was concentrated to a 200 ml volume and after settling for two hours, the top polymer phase was slowly dripped into a solution containing 400 ml methanol and 100 ml water. The bottom polymer phase was isolated by decantation. This precipitation procedure was repeated. From this procedure 64.6 g of polyamine was isolated. Elemental analysis: % C, 80.62; % H, 11.66; % N, 6.62.

An 84.5 g sample of a 29.6 wt. % solution of the above polyamine (25 g of polyamine) in toluene was added to a Fischer-Porter bottle that was equipped with a stir bar. The solution was concentrated to 50 g by means of a vacuum and the evacuated vessel was brought into the dry box. Dry toluene was added in order to prepare a 50 wt. % solution. Next 0.125 g tristriphenylphosphine rhodium chloride and 12.5 g chlorodimethylsilane were added to this solution. After capping and removing the reactor from the dry box, the solution was heated to 100° C. for 17 hours. The solution was transferred to a dry 250 ml roundbottom flask in a dry box. The solution was concentrated to 37.6 g (to remove unreacted silane) and diluted with 100 ml dry tetrahydrofuran. $^1$H NMR indicated 2.0% chlorosilane incorporation.

The above chlorosilylated polyamine in THF was diluted with 100 ml of DMF (dried over alumina). After 1 hour 0.090 g imidazole (1.3 mmoles) in 5 ml of THF was added slowly and dropwise (other amines can also be present such as triethylamine). After 15 minutes 0.5 g of misoprostol (1.3 mmoles) in 5 ml THF was added and rinsed into the solution with 2 ml THF. After stirring for 6 hours, 0.583 g imidazole (8.56 mmole) in 15 ml THF was added dropwise with stirring. Next 0.411 g methanol in 2 ml THF was added and allowed to stir for 16 hours. After adding an additional one ml of methanol the product solution was evaporated to remove all of the THF. The remaining DMF/polymer solution was allowed to stand for 1 hour in order to phase separate the polymer from the DMF solvent. The top polymer layer was separated and further dried by vacuum to remove trace DMF. From this procedure 20.6 g of polymer product was isolated.

The above polymer in THF (27.5 wt. % solution) was stirred in a 250 ml roundbottom flask. Next 1.497 g (8.55 mmoles) of α,α'-dichloro-p-xylene in 10 g THF was added dropwise to the stirred polymer solution. The product set up in 4 hours and was allowed to stand at room temperature for 20 hours. The solid product was removed with a spatula and divided into three equal parts. Each portion was washed by the following procedure by use of a wrist shaker:

a) Shaken with 200 ml THF for 0.5 hrs. and filtered and the collected solid was washed in the same manner.
b) THF was removed from the filtered polymer by vacuum.
c) The polymer was washed twice with nanopure water as in procedure a).
d) Repeated a) twice
e) The collected portions were combined and dried for 4 hours under vacuum.

From this procedure 17.5 g of crosslinked polyamine were isolated. Elemental analysis: % C, 77.3; % H, 11.4; % N, 5.65; % Cl, 3.51.

The product was evaluated for swelling. The product was found to swell at a pH of about 1 to 7. Reaction of a 25 mg sample of this material with 3 ml methanol and 3 ml pH 1 acid resulted in release of the misoprostol by HPLC.

EXAMPLE 2

This example illustrates a drug delivery system wherein misoprostol, incorporated in the crosslinked polyamine system of Example 1 is further modified by quaternization.

An 8 g sample of the crosslinked polyamine from Example 1 and 160 ml of dry THF were stirred in a 16 oz. Fischer-Porter bottle for 4 hours. Next 9 ml of dry methyl chloride was added at −78° C. After stirring for 64 hours and after removing the methyl chloride by degassing, the polymer product was filtered. After drying by vacuum, 9.7 g of methylated product was isolated. % C, 68.11; % H, 10.60; % N, 4.99; % Cl, 11.01. A 9.53 g sample of the crosslinked polymer was milled at liquid nitrogen temperature for 5 minutes to obtain 9.33 g of a fine powder. The milled material was placed in a mortar and 9.33 g of hydroxypropylmethylcellulose were added and mixed well with a pestle. This material was transferred to the mill at room temperature and ground for 3 minutes. This formulation was ball milled for 9 hours and sieved with a 250 micron sieve. From this procedure 17.4 g of polymer product (<250 micron) was recovered.

The methylated (quaternized) product was evaluated for swelling. The methylated product was found to swell within the pH range of about 1 to 8. Reaction of a 50 mg sample of this material with 3 ml methanol and 3 ml pH 1 acid resulted in release of the misoprostol as determined by HPLC. Reaction of a 50 mg sample of this material with 3 ml methanol and 3 ml water at pH 7 resulted in no detectable release of the misoprostol after 1 hour as determined by HPLC.

EXAMPLE 3

This example illustrates a drug delivery system wherein misoprostol is incorporated into a polyamine utilizing a silyl ether linker system where misoprostol is first attached to a linker via a silyl ether bond and then the misoprostol-linker system is attached to the polymer backbone. After misoprostol is attached to the polyamine via the linker, the polymer is crosslinked and milled by the same procedure as used in Example 2. This method of attaching misoprostol through a linker is also applicable for attaching a hydroxyl bearing drug to polymers such as cellulose and polysaccharides(chitosan) that do not contain carbon-carbon double bonds.

The hydroformylation reaction was carried out in a 300 ml autoclave equipped with a magnedrive stirrer. A solution of 75 g of LX-16 polybutadiene and 108 g of toluene was poured into the clave under nitrogen. Next 3.2 g of triphenylphosphine and 0.07 grams of hydridorhodiumcarbonyltristriphenylphosphine were added to the clave. The clave was sealed and further degassed with $N_2$ by pressuring the clave with 200 psi $N_2$ and then venting off the $N_2$ gas. The clave was heated to 80° C. under 400 psi $N_2$. After removing the $N_2$ the clave was charged with 300 psi 1:1 $CO/H_2$ at 80° C. The reaction was stirred at 1200 rpm for 21.5 hours at which time 3179 psi of $CO/H_2$ gas was reacted. $^1$H NMR indicated that 56% of the polybutadiene units were hydroformylated. The product solution was filtered through a millipore filter and the filtrate was concentrated to a 300 ml volume by means of a rotary evaporator. The solution was divided into 3 portions and each portion was precipitated from methanol using the following procedure:

1. The solution was dripped into a stirred solution of 200 ml of methanol and 50 ml of water.
2. The top layer was decanted and the bottom polymer layer was redissolved in 150 ml toluene.
3. Steps 1 and 2 were repeated.

From this procedure, 93 g of hydroformylated polymer product was isolated.

A solution of formyl-functionalized polymer (20 g) in 100 ml of sieved dried toluene and 10 ml methanol was placed in a 2 liter 3-neck roundbottom flask equipped with a thermometer, addition funnel and a magnetic stir bar. The solution was further diluted with 225 ml of tetrahydrofuran and 20 ml of methanol. After cooling to 5° C. under nitrogen 38.15 g of dimethylamine was added with stirring. After 15 minutes and by means of an addition funnel 58.75 ml of a 4.5M HCl/dioxane solution was slowly added to the solution. Finally 12.38 g of sodium cyanoborohydride was added by means of a funnel and rinsed into the flask with 20 ml of tetrahydrofuran. The solution was stirred for 40 hours and allowed to warm slowly to room temperature. The polymer solution was filtered after it was stirred with 100 ml of water for one hour. The filtrate formed two layers after settling for 30 minutes. After removing the lower water layer the top polymer layer was concentrated to a 150 ml volume. Next, 500 ml of a 4/1 methanol/water solution was slowly added to the polymer/THF solution and after 2 hours a polymer precipitate was formed. This precipitation procedure was repeated three times. The bottom polymer phase was isolated by decantation and after removing the solvents 11.4 grams of polyamine was isolated. % C, 77.85; % H, 11.78; % N, 8.01.

A vial was charged with 40.0 mg misoprostol (0.104 mmol) and a stir bar. After transferring to the dry box 620 mg DMF and 21.4 mg (0.315 mmol) of imidazole were added. In another vial, 26 mg (0.1046 mmol) of 1-(dimethylchlorosilyl)-2-(m,p-chloromethylphenyl) ethane (linker) was dissolved in 370 mg DMF. This linker/DMF solution was added to the stirred misoprostol/imidazole solution and stirred for 1.5 hours.

Then 9.83 g of a 20.35 wt. % solution in THF (2 g of polymer) was poured into a 100 ml roundbottom flask. 4 g of DMF (dried over alumina) was added and the THF was removed by vacuum until polymer began to fall out of solution. A few drops of THF were added to obtain a clear homogeneous solution. The final mixture was composed of 2 g of polymer, 4 g of DMF and 4.78 g THF. Next the misoprostol-linker system was added to this solution and stirred for 4 hours at room temperature.

In the dry box 0.156 g of $\alpha,\alpha'$-dichloro-p-xylene (0.886 mmoles) was dissolved in 1 g THF. After removing this solution from the dry box, this solution was added to the polymer solution. The system was allowed to crosslink for 60 hours.

The crosslinked polymer was washed by the following procedure by use of a wrist shaker:

a) Shaken with 200 ml THF for 0.5 hrs. and filtered, which wash step was repeated.

b) Removed THF from the filtered polymer by vacuum.

c) Washed with ethyl acetate as in procedure a), twice.

d) Repeated a), twice.

e) Dried for 4 hours under vacuum.

An 8 g sample of crosslinked polyamine and 160 ml of dry THF were stirred in a 16 oz. Fischer-Porter bottle for 4 hours. Next 9 ml of dry methyl chloride was added at $-78°$ C., stirred for 64 hours and the polymer filtered after removing the methyl chloride by degassing.

Cryogenic Grinding Procedure

This procedure can be employed for either the crosslinked polyamine system or the methylated product. A 9.53 g sample of the crosslinked polymer was milled at liquid nitrogen temperature for 5 minutes to obtain 9.33 g of a fine powder. The milled material was placed in a mortar and 9.33 g of hydroxypropylmethylcellulose was added and mixed with a pestle. The product was transferred to the mill at room temperature and ground for 3 minutes. This formulation was ball milled for 9 hours and sieved with a 250 micron sieve. Reaction of a 50 mg sample of this material with 3 ml methanol and 3 ml pH 1 acid resulted in release of the misoprostol by HPLC.

EXAMPLE 4

This example illustrates a drug delivery system wherein misoprostol is incorporated into a crosslinked polyamine utilizing a silyl ether linker system wherein misoprostol is first covalently bonded to a linker via a silyl ether bond, then the misoprostol-linker system is attached to the previously crosslinked polymer. The procedure described in this example could be used for bonding a drug to naturally occurring polymers such as chitosan.

A crosslinked polyamine matrix was prepared using a 13 g sample of a polyamine prepared by functionalizing a polybutadiene as described in Example 1. The polyamine was crosslinked with 1.12 g $\alpha,\alpha'$-dichloro-p-xylene in 30.3 g THF at room temperature for 48 hours. After washing the crosslinked matrix as described in Example 1, a 0.948 g sample of the crosslinked polymer and 31 ml THF was stirred overnight in a 100 ml roundbottom flask. The linking group having been covalently bonded to misoprostol in the manner described in Example 3, misoprostol reacted with 1-(dimethylchlorosilyl)-2-(m,p-chloromethylphenyl) ethane (linker), in an amount of 45 mg was added to the stirred mixture of the crosslinked polymer. After 48 hours, 10 ml of DMF was added. The reaction mixture was stirred for an additional 48 hours. The product mixture was washed with 60 ml of THF and dried under vacuum. Reaction of a 25 mg sample of this material with 3 ml methanol and 3 ml pH 1 acid resulted in release of the misoprostol.

EXAMPLE 5

This example illustrates a drug delivery system according to the teachings of the present invention wherein a drug is incorporated into a polymeric material by way of an acid sensitive linker. More particularly, this example illustrates a drug delivery system wherein misoprostol is incorporated into hydroxypropylmethylcellulose utilizing an acid-sensitive silyl ether linker.

This example also illustrates the use of natural occurring polymers as the base for the subject delivery systems. The procedure in this example could be applied to a wide variety of soluble and insoluble, naturally occurring polymer systems such as amino-celluloses and proteins, e.g., chitosan.

21.5 mg Misoprostol (0.0523 mmol) were weighed out in a vial and transferred to the dry box. Next 600 mg DMF and 3.5 mg imidazole (0.05 mmol) were added and stirred until dissolved. Finally 10.7 mg of 1,1,4,4-tetramethyl-1,4-dichlorodisilylethylene was added and stirred for 0.5 hours. In the dry box, 1 gram of hydroxypropylmethylcellulose, a stir bar and 30 ml dry THF were added to a 100 ml flask. Next 3.5 mg of imidazole and 1 ml of DMF were added to the solution. The reaction product from the above step, the misoprostol disilylchloride linker, was added and stirred for 18 hours. The solution was stripped to dryness and washed with 100 ml of toluene and filtered. The resulting white solid was dried in a vacuum.

In this manner, misoprostol is attached covalently to the hydroxypropylmethylcellulose by reaction with a disilyl-chloride linker. The product is soluble in methanol and HPLC analysis of a methanol solution indicates that no unbound misoprostol is present. Reaction of this product in a pH 1.18 methanol solution indicated release of the misoprostol from the cellulose matrix.

EXAMPLE 6

A series of the product polymer material containing misoprostol from Example 1 was made in which the amount of crosslinking was varied and swelling was studied as a function of percent crosslinking. Results, shown in Table 1, confirm that by varying the amount of crosslinking, the degree of swelling can be controlled. The rate of release of a drug can be modulated by varying the extent of swelling which is effected by varying the extent of crosslinking. The rate of release of the drug varies directly with the extent of swelling.

TABLE 1

| Amount of Crosslinking $\frac{\text{milliequivalents of Crosslinker}}{\text{milliequivalents of nitrogen}} \times 100$ | % Increase in Weight at pH 1.18 |
|---|---|
| 10.84 | 525 |
| 13.85 | 435 |
| 17.35 | 289 |
| 35.28 | 112 |

EXAMPLE 7

A series of crosslinked polyamines (containing about 10% crosslinking) prepared by the method in Example 1 and containing 30%, 50% and 70% amine functional groups were evaluated for degree of swelling at a pH of about 1. It was determined that the higher the amine functional density, the larger the degree of swelling. Results are reported in Table 2. The rate of release of drug varies directly with the extent of swelling.

TABLE 2

| % Amine | Amount of Crosslinking $\frac{\text{mequiv. crosslinking}}{\text{mequiv. of nitrogen}} \times 100$ | % Increase in Volume at pH 1.18 |
|---|---|---|
| 30 | 10.8 | 150 |
| 50 | 10.0 | 200 |
| 70 | 9.4 | 700 |

EXAMPLE 8

This example illustrates a drug delivery system wherein enisoprost is incorporated into the crosslinked polyamine system of Example 2, utilizing a silyl ether linker system.

A 23.78 g sample of a 21.03 weight percent solution of the polyamine (5 g of polyamine) prepared by functionalizing a polybutadiene polymer as described in Example 1, in toluene was added to a Fischer-Porter bottle equipped with a stir bar. The solution was adjusted to 50 weight percent by evaporating the solvent. Tristriphenylphosphine rhodium chloride was added in an amount of 0.025 g and 2.5 g of chlorodimethylsilane was also added to the solution. After capping the reactor, the solution was heated to 100° C. for 17 hours. The reaction mixture was transferred to a dry 250 ml roundbottom flask in a dry box. The solution was concentrated to a 66 weight percent solution by vacuum and diluted with 20 ml dry THF and 20 ml of dry DMF. After 15 minutes 0.0168 g imidazole in 0.562 g THF was added slowly. After 5 minutes 0.0945 g of enisoprost (0.247 mmoles) in 0.562 g of THF was added and rinsed in another 0.562 g THF. The flask was capped and stirred for 16 hours.

To the solution was added 0.14 g of imidazole in 1 ml of THF and after stirring 0.236 g of methanol in 1 ml of THF was added. After stirring for 1 hour the product solution was evaporated to remove the THF and the polymer/DMF solution was allowed to stand for 1 hour in order to phase separate the polymer from the DMF. The polymer layer was dissolved in 20 ml of THF and 10 ml of DMF was added. The polymer system with the covalently bound enisoprost was isolated by removing the THF and phase separating from the DMF. The polymer/enisoprost system was dried by vacuum. The polymer/enisoprost system was crosslinked and methylated using the procedure described in Examples 1 and 2. When exposed to a solution of pH 1 acid the enisoprost was released from the polyamine polymer.

EXAMPLE 9

Two grams of the silyl chloride polymer of Example 2 in THF solution was placed in a 100 ml round bottomed flask with a stir bar. DMF (8.4 ml) was added and the solution was stirred for 5 min. Imidazole (16 mg) was dissolved in 10 ml THF and slowly added to the polymer solution and stirred for 25 min. A solution of 78.2 mg of the compound having the following structure in 5.5 ml THF was added slowly to the stirred polymer solution and the reaction mixture was stirred for 16 hrs. Methanol (1 ml) was added and the solution was reduced in volume by rotary evaporation. The concentrated solution was added to a 30 ml separatory funnel and washed with 10 ml of DMF. The polymer was allowed to phase out of the DMF (15 min). Next the polymer was dried under vacuum and crosslinked and methylated as described in Examples 1 and 2. No free compound of the above structure was found in the THF after washing the final crosslinked methylated polymer with THF. Upon exposure to a pH 1 acid, the compound of the above structure was slowly released from the polymer: at 10 min 0.0966 mg of the compound was released from 25.6 mg polymer; at 24 hrs., 0.1968 mg of the compound was released.

EXAMPLE 10

In a dry box, a 5 g sample of a polyamine prepared by functionalizing a polybutadiene polymer as described in Example 1 and 4.3 g of dry toluene were added to a 3 oz. Fischer-Porter bottle. A 0.025 g amount of chlorotristriphenylphosphine in an additional 3 g of toluene was added to the reaction mixture. While stirring, 2.5 g of chlorodimethylsilane was added and after stirring for 2 hours at room temperature the reaction mixture was heated to 100° C. for 17 hours. The resultant product was transferred to a 250 ml flask with THF and concentrated to 66.6% solution before adding 20 ml dry THF and 20 ml of dry DMF. Next 0.166 g (2.44 mmoles) of imidazole in 0.5 ml of THF was added and stirred for 5 minutes. Following stirring, 0.627 g (2.44 mmoles) of metronidazole was added in 1 ml of THF and the solution was stirred overnight.

The polymer product was isolated by removing the THF and separating the polymer from the DMF. The polymer product was redissolved in 10 ml THF and 10 ml of DMF and the polymer was again isolated by removal of the THF layer. The polymer was then crosslinked as described in Examples 1 and 2. Reaction of a 25 mg sample of this material with 3 ml methanol and 3 ml pH 1 acid results in release of the metronidazole.

EXAMPLE 11

Alternate Crosslinker:
1,3,5-Tris(chloromethyl)benzene

The misoprostol-bound polyamine was prepared as in Example 1 and 3 grams of this polymer was diluted with THF to obtain 10.12 g of a THF solution. Next 0.311 g of 1,3,5-Tris(chloromethyl)benzene in 1 ml THF was added to this solution. An additional 0.5 g THF was added. The solution was allowed to set for 54 hours to crosslink the polymer. The crosslinked polymer was ground in an analytical mill at room temperature for 5 minutes. The resultant ground crosslinked polymer was transferred to a 2-liter beaker and stirred with 1-liter of THF for 1 hour. The reaction mixture was allowed to settle and was filtered with a glass frit buchner funnel. The cleanup step was performed for a total of 5 washes with THF, resulting in 3.1 g of crosslinked polymer, which was isolated. Elemental analysis: % C, 73.91; % H, 11.0; % N, 4.65; % Cl, 4.93.

The crosslinked polyamine was methylated as in Example 2. Elemental Analysis % C, 65.93; % H, 11.04; % N, 4.14; % Cl, 11.15.

|  |  | (Vol)<br>Wgt before swelling | (Vol)<br>Wgt after swelling |
|---|---|---|---|
| Swelling Studies: | pH 7 | 50.3 mg (5 mm) | 242.6 mg (10 mm) |
|  | pH 1 | 49.5 mg (6 mm) | 362.0 mg (14 mm) |

Volume change in parenthesis (mm)

The crosslinked product was found to swell at pH 1 to 7. The crosslinked product was mixed with 50% HPMC as described in Example 2. Reaction of a 50 mg sample of the crosslinked product with 3 ml methanol and 3 ml pH 1 acid resulted in release of misoprostol, as measured by HPLC. (100% released in the first hour.) Reaction of a 50 mg sample of the crosslinked product with 3 ml methanol and 3 ml pH 7 water resulted in a 1.73% release of the misoprostol in the first hour.

EXAMPLE 12

Change in % Crosslinking:

Example 1 was followed but instead of using 10 mole % of α,α'-dichloro-p-xylene, 17 mole % was used. Thus, 3 g misoprostol-bound polyamine in 7.12 g of THF was reacted with 0.414 g of α,α'-dichloro-p-xylene for 54 hours. After clean-up procedure was performed as in Example 1, the elemental analysis of the crosslinked polymer was as follows:

% C, 73.91; % H, 11.01; % N, 4.65; % Cl, 4.65.

The material was methylated as in Example 2, yielding an analysis as follows:

% C, 65.68; % H, 10.92; % N, 4.09; % Cl, 10.39.

Swelling Data:

|  | Before | | After | |
|---|---|---|---|---|
|  | Example 1<br>10 Mole %<br>Crosslinker | 17 Mole %<br>Crosslinker | Example 1<br>10 Mole % | 17 Mole % |
| pH 1 | 49.7 mg | 50.6 mg | 252.8 mg | 242.6 mg |
| pH 7 | 49.6 mg | 49.5 mg | 541.1 mg | 362.0 mg |

Mix with 50% HPMC.

Reaction of 50 mg of this material with 3 ml of methanol and 3 ml pH 1 acid resulted in release of misoprostol.

EXAMPLE 13

Alternate Crosslinker:
1,6-Dibromohexane

Same procedure employed as with the preparation and use of the crosslinker 1,3,5-tris(chloromethyl) benzene in Example 11. In a 100 ml r.b. flask, 2.21 g of misoprostol-bound polyamine was added (7.45 g of 29.63 wgt % solution in THF). To the flask was added, with stirring, 0.25 g (0.00103 moles) of 1,6-dibromohexane in 1 ml THF. The crosslinking reaction was permitted to occur for 54 hours. A clean-up procedure as in Example 1 was followed. Elemental analysis: % C, 73.12; % H, 11.63; % N, 4.97; % Br, 5.92.

The crosslinked polyamine was methylated, in accordance with the procedure in Example 2. Elemental Analysis: % C, 64.93; % H, 11.38; % N, 4.06; % Br, 2.53; % Cl, 9.74.

Swelling Data:

|  | Before mg (mm) | After mg (mm) |
|---|---|---|
| pH 1 | 48.8 mg (6 mm) | 296.8 mg (14 mm) |
| pH 7 | 49.5 mg (6 mm) | 910.1 mg (22 mm) |

EXAMPLE 14

Phenylmethylchlorosilyl Linker

A 34.88 g aliquot of polyamine solution (10 g of polyamine in toluene) was added to a Fischer-Porter bottle that was equipped with a stir bar. The solution was concentrated and adjusted to 50 wgt % in toluene. After transferring to a dry box, 0.1 g of chlorotristriphenylphosphinerhodium chloride was added to the polyamine solution and stirred for five minutes. Next 0.852 g of phenylmethylchlorosilane was added. After capping and removing the reactor from the dry box, the solution was heated at 100° C. for 17 hours. In a dry box reaction solution was transferred to a 250 ml r.b. flask and diluted to 50 g with THF. After adding 25 g DMF and stirring for 0.5 hours the THF and toluene were removed by vacuum. The polymer mixture was transferred to a separatory funnel. After phase separation, the bottom DMF phase was removed. The polymer was dissolved in 50 g THF and stirred with 40 g DMF for 0.5 hours. The THF was removed by vacuum and the polymer phase was separated. The resulting phenylmethylchlorosilylated polymer (9.83 g) was diluted with 34.95 g of THF and 37.06 g of DMF. Next 0.109 g triethylamine (0.514 mmole), 0.35 g of imidazole (0.514 mmols) and 0.197 g of misoprostol were added (0.514 mmoles). This solution was stirred for 17 hours. After 17 hours, 0.298 g triethylamine, 0.2 g imidazole and 0.417 g methanol was added and stirred for 1 hour. The product solution was then evaporated to remove all of the THF and allowed to stand for 1 hour to phase separate the polymer from the DMF solution. The crosslinking procedure and methylation procedure were followed according to Examples 1 and 2.

Elemental Analysis % C 75.48; % H 10.52;
after crosslinking % N, 5.41; % Cl 3.49
After methylation % C, 68.60; % H 10.89; % N, 4.46; % Cl 11.45

Reaction of a 50 mg sample of the methylated material with 3 ml methanol and 3 ml pH 1 acid resulted in release of misoprostol as monitored by HPLC (80% release after 1 hour). Reaction of a 50 mg sample with 3 ml methanol and 3 ml pH 4 acid resulted in 1% release of misoprostol after 2 hours.

EXAMPLES 15 THRU 18

For the following examples 15 through 18, the procedure from Example 14 was followed except the following indicated silane linking agents were substituted for the phenylmethylchlorosilyl linker used therein.

layer was filtered with a medium porosity glass-fritted Buchner funnel and rotovap at 50° C. with toluene to remove residual DMF.

c.) Hydrosilylation of the polyamine.

10 g polyamine (34.88 g polyamine/toluene solution) was placed in a 6 oz. Fischer-Porter bottle. After capping, most

ELEMENTAL ANALYSIS

| EXAMPLE | SILANE (gms) | CROSSLINKED | | | | METHYLATED | | | | % Released in 1 hr. pH 1 Misoprostol | % RELEASED in 1 hr at pH 6–7 Misoprostol |
|---|---|---|---|---|---|---|---|---|---|---|---|
| | | % C | % H | % N | % Cl | % C | % H | % N | % Cl | | |
| 15 | Ph₂SiHCl (1.19 g) | 75.91 | 10.90 | 5.17 | 3.60 | 69.41 | 10.42 | 4.14 | 11.72 | 62% | Trace too small to quantity (pH 7) |
| 16 | PhSiEtHCl | 76.96 | 1.57 | 531 | 3.90 | 9.09 | 11.33 | 4.71 | 10.99 | Releases at pH 1 | — |
| 17 | Diisopropylchlorosilane | 76.6 | 11.78 | 5.42 | 3.73 | 69.09 | 11.32 | 4.71 | 10.99 | ~5% | None detected by |
| 18 | Et₂SiHCl (2.58) | 75.1 | 11.43 | 5.08 | 3.65 | 57.0 | 9.41 | 3.70 | 9.37 | 83% | None detected by HPLC (pH 6) |

*50 mg sampie in 3 ml acid and 3 ml methanol.

EXAMPLE 19

1. Procedures for Single Isomer with Isopropyl ethyl crosslinker a.) Hydroformylation of polybutadiene.

Under a stream of nitrogen, a 2.0 liter autoclave was charged with 289.0 grams of polybutadiene, 308 ml of toluene, 12.7 g triphenylphosphine, and 0.27 g of hydridocarbonyl tristriphenylphosphinerhodium. The reaction was heated to 80° C. under nitrogen and then charged with 300 psi of CO/H$_2$ and stirred at 1000 rpm's until the 33.5% of the butadiene units were hydroformylated. The reaction was substantially complete in approximately 3.5 hours. The proton NMR confirmed the extent of reaction. The reaction mixture was removed from the clave and toluene was used to aid in the transfer. The solution was filtered to remove particulates and concentrated to 500 g. A 250 gram portion of this solution was slowly dripped into 1000 ml of methanol/water (80/20, v/v) with stirring. After stirring for an additional 15 minutes, the stirring was stopped, and the reaction mixture was let set for 1 hour. The bottom polymer layer was isolated and the washing step was repeated. The dry polymer was redissolved in toluene and stored in the dark.

b.) Reductive amination of the polyaldehyde to the polyamine.

Toluene was removed from the polyaldehyde by means of a vacuum. Next the polyaldehyde (300.29 g) was diluted with 785 ml of DMF. The mixture was divided into two separate batches for reductive amination. A 2 liter clave was charged with 150 grams polyaldehyde in 392.5 ml DMF, 330 ml cyclohexane, 112 g dimethylamine and 1.5 g ruthenium carbonyl. The clave was sealed and quickly purged with 100 psi CO/H$_2$. The clave was charged with 100 psi of CO/H$_2$ and 900 psi of H$_2$. The clave was heated to 120° C. at 1000 rpm's. Gas uptake was initiated at about 30° C. Reaction was completed when gas uptake stopped. The reaction was complete in approximately 2 hours. After cooling to room temperature, the contents were removed from the clave and placed in a 1 liter separatory funnel and allowed to phase out. The lower reddish-brown DMF level was removed and discarded. To a separatory funnel was added 300 ml of DMF and cyclo-hexane to make the original volume. The separation procedure was repeated. The DMF extraction procedure was performed a total of three times. The cyclohexane of the toluene and air were removed by vacuum distillation with stirring. The reactor was placed into a dry box and 0.1 g chlorotristriphenylphosphinerhodium and 9.58 g toluene were added to bring the solution to 50 wgt %. Next, 0.741 g of isopropylethylchlorosilane was added. The reactor was capped and heated at 100° C. by means of a temperature controlled oil bath for 17 hours. The reaction was transferred to a dry box and the solution transferred to a dry 250 ml r.b. flask equipped with stir bar. The reactor was washed with dry THF and a total of 50 g THF was added to the reaction product. Next, 50 ml dry DMF were added and stirred for 0.5 hrs. The THF and toluene were removed by vacuum, and the polymer separated from the remaining DMF solution. The reaction mixture was poured into a 125 ml separatory funnel and allowed to phase out for 1 hour. The lower DMF layer was removed. The polymer was redissolved with 50 g dry THF. 40 g of DMF was added, and the wash procedure repeated along with the separation procedure. The polymer was redissolved in 100 ml of dry cyclohexane and extracted with 80 ml of DMF. 20 ml of cyclohexane was added to the cyclohexane phase and again extracted with 80 ml of DMF. The clean polymer was stored in dry THF.

d.) Coupling of single isomer of misoprostol to the silylchloride polymer.

The silylchloride polymer was concentrated to 80 wgt. % (total of 16.014 g polymer) and 57 g THF and 60.5 g DMF were added. With stirring, 0.022 g triethylamine in 0.3 g THF and 0.008 g imidazole in 0.3 g THF were added. Next 0.0441 g of the single bioactive isomer (11R, 16S) of misoprostol, having the following structure:

was added and stirred for 20.5 hours at room temperature. The coupling was monitored by TLC. The reaction was quenched by adding 0.87 g triethylamine, 0.583 g imidazole and. 1.4 g methanol and stirred for 1 hr. After removing from the dry box, the THF was removed by distillation and the remaining solution was transferred to a separatory funnel and allowed to phase out for 1 hour. The polymer was redissolved in 85 ml THF and 60 ml DMF and stirred for 0.5 hrs. The THF was removed and the DMF was separated from the polymer by means of a separatory funnel. 14.21 g of polymer were recovered.

e.) Crosslinking of the single isomer of misoprostol-prepolymer.

The prepolymer from step (d) (14.2 g) was dissolved in 33.2 g of THF and then 1.13 g of α,α'-dichloro-p-xylene were added and allowed to stir until it crosslinked. The reaction was allowed to set for 60 hours. The crosslinked polymer was cut with a spatula and ground in an analytical mill. The polymer was stirred with 1400 ml of THF and filtered with a 600 ml coarse filter. The washing procedure was repeated five times. Elemental analysis: % C, 74.01; % H, 11.15; % N, 5.28; % Cl, 3.86.

f.) Methylation of the crosslinked polyamine.

The THF wet cake from the previous step (e) was placed in a 12 oz. Fischer-Porter bottle with a stir bar. HPLC grade THF was added to give a total volume of 245 ml (premeasured on bottle). The bottle was capped, the solution was stirred and cooled to dry ice temperature for 0.5 hours. Methylchloride was added until the volume increased by 20% (up to a premeasured volume of 294 ml. The solution was stirred for 60 hours. The reactor was vented and purged with nitrogen. Using a coarse filter, the mixture was filtered and then washed with 1400 ml of THF. After filtering, the residue was dried on a vacuum line for 6 hours. A small sample was removed and dried overnight at 50° C. for elemental analysis: % C, 67.245; % H, 10.96; % N, 4.52; % Cl, 11.41; Cl/N=0.997

The polymer was placed in an analytical mill fitted with a cryogenic top. The mill was placed in a glove bag and while under nitrogen, the polymer was ground at liquid nitrogen temperature. The ground polymer was allowed to warm under nitrogen to prevent moisture build up. The ground polymer was sieved with 250 micron sieve and the 250 micron material (13.84 g) was mixed with 13.84 g of HPMC. The mixture was mixed in an analytical mill for 1 minute. The mixture was transferred to a ball mill and milled for 12 hours. The resultant mixture was sieved through a 250 micron filter. The collected polymer (26.86 g) was placed in an amber bottle and stored in a freezer.

EXAMPLE 20

Synthesis of Diisopropyl Drug Delivery System with Single Isomer Misoprostol a.) Hydrosilylation of polyamine.

12.0 g of polyamine (33.5% amine; 28.67 wt % in toluene) was weighed out in a tared 6 oz. Fischer-Porter bottle containing a magnetic stir bar. The Fischer-Porter bottle was sealed and the toluene was removed in vacuo. The Fischer-Porter bottle was taken into a dry box still under vacuum. The polymer was redissolved to 50 wt % in toluene with 12.0 g of toluene and 0.120 g of chloro-tris (triphenylphosphine)rhodium(I) (Strem Chemical) was added to the polymer solution. Diisopropylchlorosilane (0.981 g, 6.52 mmol; Huls America) was weighed out in a vial and added slowly to the polymer solution. The Fischer-Porter bottle was sealed and removed from the dry box. The Fischer-Porter bottle was placed in a temperature controlled oil bath at 100° C. and stirred for 24 hrs.

b.) DMF wash after hydrosilylation.

After 24 hrs., the Fischer-Porter bottle was removed from the oil bath and transferred to the dry box. The polymer solution was transferred to a 250 ml round bottom flask with a magnetic stir bar. Dry tetrahydrofuran (THF) was added to the solution to make 50 g of solvent. 25 g of DMF was added to the polymer solution and the solution was stirred for 30 minutes. The THF and toluene was removed in vacuo and the polymer-DMF mixture was transferred to a 125 ml separatory funnel and allowed to phase separate for 17 hrs. The lower layer (DMF) was drained into a small bottle. The upper layer (polymer) was washed back into the 250 ml round bottom flask with 50 g of THF. To the THF-polymer solution, 40 g of DMF was added and the solution was allowed to stir for 30 minutes. The THF was removed in vacuo and the DMF-polymer mixture was transferred to a 125 ml separatory funnel and allowed to phase separate for 17 hrs. The lower (DMF) layer was drained into a small bottle and the polymer was washed back into the 250 ml round bottom flask with THF.

c.) Coupling of single isomer Misoprostol- to the Silyl Chloride Polymer.

The polymer-THF solution was concentrated in vacuo to 80 weight percent. The solution was diluted with THF (4 ml/g of polymer) and DMF (4 ml/g of polymer) and transferred to a 250 ml, 3 neck flask. To this solution, triethylamine (0.03 g, 0.30 mmol), DMAP (0.0375 g, 0.30 mmol), and single isomer misoprostol (0.060 g, 0.15 mmol) was added. The flask was capped with rubber septa and removed from the dry box. The flask was placed in a temperature controlled oil bath at 50° C. for 20 hours. Coupling of drug to the polymer was monitored by Thin Layer Chromatography (TLC). After 20 hours, the reaction was quenched by addition of triethylamine (0.42 g), DMAP (0.50 g), and methanol (0.66 g) which converts all of the remaining silyl chloride groups on the polymer to silylmethoxy groups. This solution was stirred for 1 hour and the THF was removed in vacuo. The DMF-polymer mixture was transferred to a 125 ml separatory funnel and allowed to phase out for 1 hour. The lower DMF layer was drained into a small bottle and the polymer was transferred into the 250 ml flask with 35 ml of THF. DMF (35 ml) was added to the polymer solution and the solution was stirred for 1 hour. The THF was removed in vacuo and the polymer-DMF mixture was transferred to a 125 ml separatory funnel and allowed to phase out for 1 hour. The lower DMF layer was drained into a small bottle and the polymer was redissolved in THF. The polymer solution was filtered through a coarse glass fritted funnel. The filtered polymer solution was pumped to dryness on a vacuum line. Subsequent steps, crosslinking, methylation, and grinding, were performed as detailed in the previous Examples.

EXAMPLE 21

Preparation of silyl ether product of metronidazole and phenylmethylchlorosilyl-2-(p-chloromethylphenyl) ethane:

A solution of 12.98 g phenylmethylchlorosilyl-2-(p-chloromethylphenyl)ethane in 100 ml of anhydrous dimethylformamide was dripped into a solution of 8.98 g metronidazole and 7.14 g imidazole in 400 ml anhydrous dimethylformamide at room temperature with magnetic stirring and under a positive nitrogen pressure for 20 hours.

The reaction product was isolated by pouring the reaction mixture into a separatory funnel containing 250 ml diethyl ether and 750 ml water. The ether and aqueous phases were separated, and the aqueous phase was washed 3 times with 250 ml portions of ether. The combined ether extracts were washed 5 times with 150 ml portions of water and once with a 300 ml portion of saturated aqueous NaCl solution. The ether solution was dried over $MgSo_4$, and stripped on a rotary evaporator followed by further drying on a high-vacuum line.

The crude product was taken up in methylene chloride and run on a preparative HPLC column using 10/90 and 50/50 volume percent mixtures of ethyl acetate and hexanes respectively as eluants.

Preparation of the polyamine adduct with the above silyl ether:

27.23 g (36.8 mmoles) of dry polymer was dissolved in 35 ml of anhydrous tetrahydrofuran under nitrogen. The metronidazole silyl ether product was dissolved in 12.4 ml of anhydrous tetrahydrofuran and dripped into the polymer solution at room temperature with stirring. After stirring for 24 hours, 83.4 ml of anhydrous tetrahydrofuran was added, followed in a half hour by dripping in a solution of 2.16 g of $\alpha,\alpha^1$-dichloro-p-xylene in 10 ml of anhydrous tetrahydrofuran. This was stirred for 18 hours. The reaction mixture crosslinked over-night and was left at room temperature for 5 days.

The product was worked up by grinding in an explosion-proof Waring blender containing 550 ml anhydrous tetrahydrofuran and filtering while protecting from atmospheric moisture. This was repeated one time. The finely divided product was dried on a rotary evaporator, followed by overnight drying on a high-vacuum line.

In Vitro release analysis of metronidazole at pH2:

A weighed amount (~50 mg) of the metronidazole/linker/polymer drug was slurried in 6.0 ml of dilute aqueous HCl and pH2 in a culture tube with a teflon-lined cap that was equipped with a magnetic stir bar. The slurry was stirred for given time intervals, centrifuged, and a 250 µl aliquot removed and analyzed by HPLC for metronidazole content in mg/ml.

Using this method, 3 wgt % of metronidazole was released in 30 minutes and 9.5 wgt % was released in 24 hours (wgt % of 50 mg sample).

This example demonstrates a 9.5 wgt % loading of a drug in a crosslinked polyamine.

EXAMPLE 22

The procedures of Example 15 were repeated in every essential detail, except the active ingredient was the single bioactive isomer (11R,16S) of misoprostol, as used in Examples 19 and 20. The pharmacological data for the resulting system is reported in TABLE 8.

EXAMPLE 23

The procedures of Example 20 were repeated in every essential detail with the exceptions that the linking group was chloro(t-butyl)methylsilane and the active ingredient was misoprostol. The misoprostol was released from the polymeric delivery system at pH 1 conditions.

EXAMPLE 24

The procedures of Example 20 were repeated in every essential detail with the exception that the linking group was chloroisobutylisopropylsilane. The active ingredient was the single bioactive isomer of misoprostol. The misoprostol isomer releases from the polymeric delivery system at pH 1 conditions.

Experiment 1

Plasma Concentration

Figure 1:
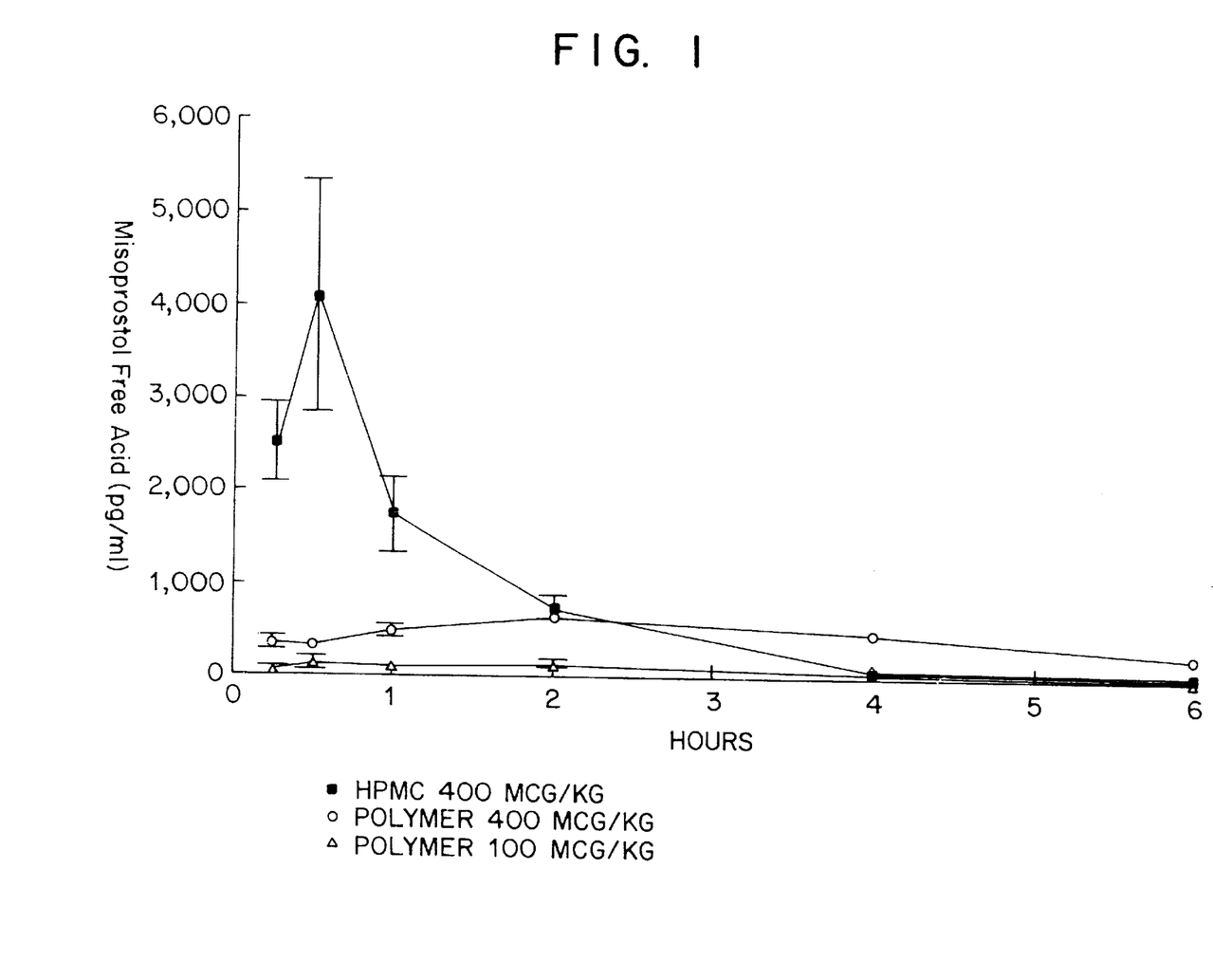

Plasma concentration of misoprostol free acid was measured for misoprostol delivered by way of a drug delivery system prepared as in Example 2. The subject system delivers misoprostol at a rate sufficient to provide local gastric therapeutic action without any significant systemic side effects, as compared to misoprostol delivered by way of a hydroxypropylmethylcellulose (HPMC) carrier wherein the misoprostol is adsorbed thereunto. The results, reported in Table 3 and illustrated in FIG. 1, show that the polymer delivery system of Example 2 reduces the peak plasma level and total systemic exposure to misoprostol free acid relative to the HPMC formulation. In addition, the polymer delivery system produced sustained misoprostol free acid plasma levels for the duration of the study (6 hours for the 400 µg/kg dosage) indicating a prolonged gastric residency and availability of misoprostol from the polymer delivery system.

TABLE 3

|  | TIME TO PEAK (HOURS) | PEAK CONCENTRATION (pg/ML)[3] | AUC[1] | % SYSTEMIC[2] EXPOSURE |
|---|---|---|---|---|
| HPMC as carrier (400 µg/Kg) | 0.5 | 4100 | 4770 | — |
| POLYMER (100 µg/Kg) | 2.0 | 131 | 402 | 8.4 |
| POLYMER (400 µg/Kg) | 2.0 | 646 | 2790 | 58.5 |

[1]Area under the plasma concentration-time curve from time 0 to 6 hours.
[2]Relative to the HPMC 400 µg/Kg dose which is considered 100%.
[3]Picograms per milliliter.

Experiment 2

Challenge Against Indomethacin-induced Gastric Mucosal Damage

Male Charles River rats [Crl:COBS,CD(SD)BR], 180–210 g body weight, were food deprived with water available ad libitum for twenty four hours before the study. On the day of the experiment, the rats were randomly divided into groups of six rats each. Misoprostol/HPMC (3, 10, 30 and 100 µg misoprostol/kg), HPMC (10.1 mg/kg), the polymer/misoprostol system of Example 2 (1, 3, 10 and 30 µg misoprostol/kg referred to in Table 4 as Ex 2 System) or the polybutadiene polymer (containing no misoprostol) of Example 2 (polymer/HPMC, 9.1 mg/kg referred to in Table 4 as Ex 2 Polymer), dissolved or suspended in distilled water, was administered intragastrically (10 ml/kg) to the groups of six rats each. Thirty minutes after dosing, each rat received 16 mg/kg indomethacin (Sigma Chemical Co.) intraperitoneally in 0.5% aqueous methylcellulose (4000 cps., Sigma Chemical Co.) solution (10 ml/kg). Five hours later, the animals were sacrificed by $CO_2$ asphyxiation. Each stomach was removed, cut open along the greater curvature, and rinsed gently with tap water. The glandular portion of the gastric mucosa was examined under a stereomicroscope at 10× magnification. Gastric lesions were counted without knowledge of the treatment. Data from two experiments were pooled and significance (P<0.05) was determined using a one way analysis of variance and Dunnett's multiple comparison procedure. The results of the experiment are presented in the following Table 4. The polymer/misoprostol delivery system, like misoprostol/HPMC exhibited activity against indomethacin-induced gastric glandular mucosal damage in the rat. The minimal effective dose was the same for each preparation, 10 µg/kg intragastrically.

TABLE 4

Effect Against Indomethacin-Induced Gastric Damage in the Rat

| Treatment | Dose (µg Miso/kg i.g.) | No. of Gastric Lesions/Rat (x ± S. E.) |
|---|---|---|
| HPMC | — | 18.2 ± 2.9 |
| Miso/HPMC | 3 | 15.0 ± 2.6 |
|  | 10 | 6.3 ± 1.8 |
|  | 30 | 4.6 ± 1.8 |
|  | 100 | 2.3 ± 0.9 |
| Ex 2 Polymer | — | 17.3 ± 2.8 |
| Ex 2 System | 1.0 | 17.1 ± 3.1 |
|  | 3.0 | 14.2 ± 2.3 |
|  | 10.0 | 8.6 ± 2.4 |
|  | 30.0 | 0.7 ± 0.3 |

Experiment 3
Challenge Against Alcohol-Induced Gastric Mucosal Damage

Twenty four hour food deprived male Charles River rats weighing 180–210 g were dosed intragastrically (10 ml/kg) with misoprostol/HPMC (100, 200, 400 or 600 µg misoprostol/kg) or HPMC (60.6 mg/kg) dissolved in distilled water or the polymer/misoprostol system of Example 2 (50, 100, 200, or 400 µg misoprostol/kg referred to in Table 5 as Ex 2 System) suspended in distilled water or the blank polybutadiene polymer (containing no misoprostol) of Example 2 (polymer/HPMC 125 mg/kg referred to in Table 5 as Ex 2 Polymer) suspended in distilled water. Four hours later, each rat received 1 ml of absolute ethanol intragastrically. One hour after ethanol administration, the rats were killed by $CO_2$ asphyxiation. The stomach of each rat was removed, opened, and gently rinsed with tap water. The glandular portion of the gastric mucosa was examined under a stereomicroscope at 10× magnification. Gastric lesions were counted by an investigator "blinded" as to treatment. Significance ($p<0.05$) was determined using a one way analysis of variance and Dunnett's multiple comparison procedure. The results are reported in Table 5.

TABLE 5

Effect Against Alcohol-Induced Gastric Damage in the Rat

| Treatment | Dose (µg miso/kg i.g.) | No. of Gastric Lesions/Rat | % Change |
|---|---|---|---|
| HMPC | — | 20.5 ± 2.0 |  |
| Miso/HPMC | 100 | 20.1 ± 2.9 | −1.9 |
|  | 200 | 15.9 ± 2.0 | −22.4 |
|  | 400 | 10.8 ± 3.3 | −47.3 |
|  | 600 | 7.3 ± 2.0 | −64.4 |
| Ex 2 Polymer | — | 24.2 ± 2.3 |  |
| Ex 2 System | 50 | 21.6 ± 2.1 | −10.7 |
|  | 100 | 16.4 ± 2.1 | −32.2 |
|  | 200 | 8.8 ± 2.6 | −63.6 |
|  | 400 | 3.0 ± 1.1 | −87.6 |

Experiment 4
Procedure for Intraintestinal Administration Diarrhea Assessment

Male Charles River rats [Crl:COBS,CD(SD)BR], 180–210 g body weight, were food deprived with water available ad libitum for twenty four hours before the study. On the day of the experiment, the rats were randomly divided into groups of six rats each. Each rat was anesthetized with methoxyflurane, the abdomen was opened, and the first part of the small intestine was exteriorized. Misoprostol/HPMC (215–1000 µg misoprostol/kg), HPMC (68.8 mg/kg), the polymer/misoprostol system of Example 2 (316–1470 µg misoprostol/kg referred to in Table 6 as Ex 2 System) or the blank polybutadiene polymer (containing no misoprostol) of Example 2 (polymer/HPMC, 445 mg/kg referred to in Table 6 as Ex 2 Polymer), dissolved or suspended in distilled water, was injected (5 ml/kg) directly into the intestinal lumen using a 23 gauge hypodermic needle. The abdominal incision was closed with wound clips and collodion. The rats were placed in individual wire mesh cages and the collection trays were lined with Kraft paper. Diarrhea was assessed on an all-or-none basis at hourly intervals for eight hours after treatment. Diarrhea was defined as unformed or watery stools that wet the paper liner. The eight hour $ED_{50}$ value for misoprostol/HPMC was calculated using a logistic regression model. The polymer/misoprostol system of Example 2 showed no diarrhea at the doses tested, indicating that no significant amount of misoprostol was released in the intestine.

TABLE 6

Diarrheagenic Activity Following Intraintestinal Administration in the Rat

| Treatment | Dose (µg Miso/kg) | No. Rats with Diarrhea (8 hr) No. of Rats Treated |  |
|---|---|---|---|
| HPMC | — | 0/6 |  |
| Miso/HPMC | 215 | 0/6 |  |
|  | 316 | 1/6 | $ED_{50} = 534$ µg/kg |
|  | 464 | 3/6 | (95% C.I.,377,757) |
|  | 681 | 4/6 |  |
|  | 1000 | 5/6 |  |
| Ex 2 Polymer | — | 0/6 |  |
| Ex 2 System | 316 | 0/6 |  |
|  | 681 | 0/6 |  |
|  | 1470 | 0/6 |  |

Experiment 5
Procedure for Intragastric Administration Diarrhea Assessment

Male Charles River rats [Crl:COBS,CD(SD)BR], 190–210 g body weight, were food deprived with water available ad libitum for twenty four hours before the study. On the day of the experiment, the rats were randomly divided into groups of three rats each. Misoprostol/HPMC (68, 100, 147, 215, 316, 464 and 681 µg misoprostol/kg), HPMC (68.8 mg/kg), the polymer/misoprostol system of Example 2 (100, 215, 316, 464, 681, 1000 and 1470 µg misoprostol/kg referred to in Table 7 as Ex 2 System) or the blank polybutadiene polymer containing no misoprostol) of Example 2 (polymer/HPMC, 445 mg/kg referred to in Table 7 as Ex 2 Polymer), dissolved or suspended in distilled water, was administered intragastrically (10 ml/kg) to the groups of three rats each. The rats were placed in individual wire mesh cages and the collection trays were lined with Kraft paper. Diarrhea was assessed on an all-or-none basis at hourly intervals for eight hours after dosing. Diarrhea was defined as unformed or watery stools that wet the paper liner. Data from two experiments were pooled and $ED_{50}$ values calculated using a logistic model. A liklihood ratio test was employed to determine if the $ED_{50}$ values were significantly different.

The results of the study are summarized in Table 7. The polymer system with misoprostol was significantly less diarrheagenic in the rat than misoprostol/HPMC, the $ED_{50}$ values being 715 and 265 μg misoprostol/kg respectively intragastrically.

TABLE 7

Diarrheagenic Activity Following Intragastric Administration in the Rat

| Treatment | Dose (μg Miso/kg) | No. Rats with Diarrhea (8 hr) No. of Rats Treated | |
|---|---|---|---|
| HPMC | — | 0/6 | |
| Miso/HPMC | 68 | 0/6 | |
| | 100 | 1/6 | |
| | 147 | 2/6 | |
| | 215 | 0/6 | |
| | 316 | 5/6 | $ED_{50}$ = 265 μg/kg |
| | 464 | 4/6 | (95% C.I.,188,388) |
| | 681 | 6/6 | |
| Ex 2 Polymer | — | 0/6 | |
| Ex 2 System | 100 | 1/6 | |
| | 215 | 1/6 | |
| | 316 | 2/6 | |
| | 464 | 1/6 | $ED_{\_\_}$ = 715 μg/kg |
| | 681 | 2/6 | (95% C.I.,378,1352) |
| | 1000 | 3/6 | |
| | 1470 | 6/6 | |

The studies reported in Table 5 herein show that the misoprostol/HPMC was active against ethanol induced gastric damage at 400 μg misoprostol/kg when administered intragastrically four hours before ethanol, whereas the polymer/misoprostol delivery system produced an equivalent effect at 100 μg misoprostol/kg suggesting sustained availability of misoprostol from the polymer delivery system of Example 2. The delivery system of Example 2 and misoprostol/HPMC exhibited the same activity against indomethacin induced gastric damage with a minimum effective dose of 10 μg misoprostol/kg for each preparation. In contrast to the efficacy studies, the delivery system of Example 2 was significantly less diarrheagenic than misoprostol/HPMC, the eight hour $ED_{50}$ values being, respectively, 715 and 265 μg misoprostol/kg as shown in Example 15. Furthermore, no diarrhea was observed by intestinal administration of the polymer/misoprostol system of Example 2, indicating that no significant amount of misoprostol was released in the intestines of the rat which is at a pH of about 7 or greater.

Although the system has been described herein with regard to specifics, other modifications can be made to the polymer system to effect changes in the rate of release of an active ingredient from the delivery system. For example, the percentage and nature of the auxiliary groups on the polymer backbone can be modified, the extent of crosslinking can be varied, and the steric and electronic environment of the hydrolyzable covalent bond to the drug can be varied (e.g., the linker group can be varied from a dimethylsilane to a diphenylsilane group or such two linkers can be employed in the same polymer delivery system to provide a sustained/controlled rate of release).

The following TABLE 8 provides the results of experiments with certain polymeric delivery systems described herein wherein the steric and electronic environment of the hydrolyzable covalent bond to the drug has been varied. The table provides the results for the specific polymer delivery systems with respect to antiulcer activity against Indomethacin gastric damage and the results from studies to define diarrheagenic activity of the delivery systems in comparison to a misoprostol/HPMC dispersion. The results show that the delivery systems retain antiulcer activity and exhibit a lower diarrheagenic side effect (i.e., the diarrhea, if any, being noted at a higher concentration for the delivery systems than for the misoprostol/HPMC dispersion).

TABLE 8

Pharmacological Summary of Silicon Substituted Polymeric Delivery Systems in Comparison to Miso/HPMC

| System | Silicon Substitution | Drug | Antiulcer Activity Indomethacin Gastric Damage ED50s | Diarrheagenic Activity μg/kg |
|---|---|---|---|---|
| Ex 1 | $Me_2$ | Miso | 9.7 | 715 |
| Miso/HPMC | | | 13.2 | 265 |
| Ex 18 | $Et_2$ | Miso | 7.7 | 910 |
| Miso/HPMC | | | 9.5 | 290 |
| Ex 14 | PhMe | Miso | 7.0 | 858 |
| Miso/HPMC | | | 7.6 | 325 |
| Ex 15 | $Ph_2$ | Miso | 16.0 | 2031 |
| Miso/HPMC | | | 27.1 | 485 |
| Ex 17 | $(Isopropyl)_2$ | Miso | 32.6 | NoDiarrheaat 1856 |
| Miso/HPMC | | | 29.5 | 430 |
| Ex 22 | $Ph_2$ | (11R,16S) Isomer* | 4.3 | 515 |
| Miso/HPMC | | | 24.9 | 316 |
| Ex 19 | Isopropyl/Et | (11R,16S) Isomer* | 4.1 | 329 |
| Miso/HPMC | | | 27.7 | 321 |
| Ex 20 | $(Isopropyl)_2$ | (11R,16S) Isomer* | 3.2 | NoDiarrheaat 467 |
| Miso/HPMC | | | 17.8 | 316 |

*Single bioactive isomer of misoprostol

What is claimed is:

1. A delivery system for releasing an active ingredient at pH values up to about 7 and for inhibiting release of the active ingredient at pH values above 7, the system, comprising a polymeric material covalently bonded to the active ingredient through a covalent bond that is pH sensitive and capable of being cleaved at pH values up to about 7.

2. A delivery system as recited in claim 1 wherein the covalent bond between the active ingredient and the polymeric material comprises an acetal, thioacetal, imine, aminal, carbonate, vinyl ether, silyl ester or silyl ether covalent bond.

3. A delivery system as recited in claim 2 wherein the polymeric material is bonded to the active ingredient through a silyl ether covalent bond.

4. A delivery system as recited in claim 3 wherein the polymeric material comprises a polymer having a silyl moiety.

5. A delivery system as recited in claim 4 wherein the polymer includes the silyl moiety in the backbone structure or along a branch of the backbone structure of the polymeric material.

6. A delivery system as recited in claim 1 wherein the polymer is substantially nonabsorbable and physiologically inactive.

7. A delivery system as recited in claim 6 wherein the polymer comprises a polymer selected from polyamines, polybutadienes, copolymers of 1,3-dienes, polysaccharides, hydroxypropylmethylcellulose, and polymers of acrylic and methacrylic acid including copolymers thereof, maleic copolymers, and a polymer having derivatizable olefinic bonds.

8. A delivery system as recited in claim 7 wherein the polymer is selected from a polyamine, polybutadiene, copolymers of 1,3-dienes and a polymer having a derivatizable olefinic bond.

9. A delivery system as recited in claim 8 wherein the polymer comprises a polyamine.

10. A delivery system as recited in claim 8 wherein the polymer comprises a polybutadiene.

11. A delivery system as recited in claim 6 wherein the polymer is crosslinked to provide the nonabsorbable property.

12. A delivery system as recited in claim 11 wherein the crosslinking agent is a dialdehyde, diacid, disilane, dihaloxylene, tri(halomethyl)benzene, dihaloalkane, dihaloalkene, diallylhalide, or any polyaromatic, aliphatic or allylic halide.

13. A delivery system as recited in claim 1 wherein the active ingredient is covalently bonded to the polymer through a linking group.

14. A delivery system as recited in claim 13 wherein the linking group comprises a group which forms a bond with the active ingredient that is an acetal, thioacetal, imine, aminal, carbonate, vinyl ether, silyl ester or silyl ether covalent bond.

15. A delivery system as recited in claim 14 wherein the linking group comprises a silyl linking group of the structure wherein P is the polymer, Y-D is the active ingredient with Y representing —O— or group; and $R_1$ and $R_2$ are independently H, or substituted or unsubstituted, alkyl, cycloalkyl, alkenyl, alkynyl, aryl, alkaryl or aralkyl groups.

16. A delivery system as recited in claim 15 wherein the linking group comprises a group which forms a silyl ether type covalent bond.

17. A delivery system as recited in claim 16 wherein the linking group is selected from chlorodiisopropylsilane, chloroisopropylethylsilane, chlorodimethylsilane, chlorodiphenylsilane, 1-(dimethylchlorosilyl)-2-(m,p-chloromethylphenyl)ethane, and 1,1,4,4-tetramethyl-1,4-dichlorodisilylethylene, chlorophenylmethylsilane, chloro(t-butyl)methylsilane, chloroisopropylisobutylsilane, and chlorodiethlylsilane.

18. A delivery system as recited in claim 17 wherein the linking group is chlorodiisopropylsilane.

19. A delivery system as recited in claim 17 wherein the linking group is chloroisopropylethylsilane.

20. A delivery system as recited in claim 1 wherein the active ingredient comprises a compound which contains a hydroxyl group, a carboxylic acid group, an amino group or an —NHR group wherein R is an alkyl group of 1–4 carbons, a thiol group, or an enolizable carbonyl group.

21. A delivery system as recited in claim 20 wherein the active ingredient contains a hydroxyl functional group.

22. A delivery system as recited in claim 21 wherein the active ingredient is selected from a natural or synthetic prostaglandin or prostacyclin.

23. A delivery system as recited in claim 21 wherein the active ingredient comprises a prostaglandin analogue of the structure wherein R represents hydrogen or lower alkyl having 1 to 6 carbon atoms; $R_1$ represents hydrogen, vinyl or lower alkyl having 1 to 4 carbon atoms and the wavy line represents R or S stereochemistry; $R_2$, $R_3$, and $R_4$ are hydrogen or lower alkyl having 1 to 4 carbon atoms or $R_2$ and $R_3$ together with carbon Y form a cycloalkenyl having 4 to 6 carbon atoms or $R_3$ and $R_4$ together with carbons X and Y form a cycloalkenyl having 4 to 6 carbons and wherein the X–Y bond can be saturated or unsaturated.

24. A delivery system as recited in claim 23 wherein the active ingredient comprises misoprostol.

25. A delivery system as recited in claim 23 wherein the active ingredient is a compound having the structural formula:

26. A delivery system as recited in claim 25 wherein the linking group is chlorodiisopropylsilane.

27. A delivery system as recited in claim 25 wherein the linking group is chloroisopropylethylsilane.

28. A delivery system as recited in claim 25 wherein the linking group is chlorodiphenylsilane.

29. A delivery system as recited in claim 23 wherein the active ingredient comprises enisoprost.

30. A delivery system as recited in claim 21 wherein the active ingredient comprises metronidazole.

31. A delivery system as recited in claim 1 wherein the polymer is adapted to swell at pH values of about 1 to 7.

* * * * *